(12) United States Patent
Lidolt et al.

(10) Patent No.: US 8,273,042 B2
(45) Date of Patent: Sep. 25, 2012

(54) ORTHOPEDIC AID WITH A LOCKING DEVICE

(75) Inventors: Klaus Lidolt, Duderstadt (DE); Matthias Schilling, Weiβenborn-Lüderode (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 227 days.

(21) Appl. No.: 10/798,845

(22) Filed: Mar. 12, 2004

(65) Prior Publication Data
US 2004/0225242 A1 Nov. 11, 2004

(30) Foreign Application Priority Data
Mar. 12, 2003 (DE) .................. 103 11 189

(51) Int. Cl.
*A61F 5/00* (2006.01)
*A61F 5/37* (2006.01)
*A61F 13/00* (2006.01)
*A61B 19/00* (2006.01)

(52) U.S. Cl. .................. 602/16; 602/2; 602/5; 602/23; 602/26; 340/870.07; 128/846; 128/869; 128/882

(58) Field of Classification Search .............. 602/2, 16, 602/26, 27, 23; 340/870.07; 128/903, 869, 128/882, 902
See application file for complete search history.

(56) References Cited

U.S. PATENT DOCUMENTS

| | | | |
|---|---|---|---|
| 3,408,660 A | 11/1968 | Walters | |
| 4,685,926 A | 8/1987 | Haupt | |
| 5,476,441 A * | 12/1995 | Durfee et al. | 602/23 |
| 5,484,389 A * | 1/1996 | Stark et al. | 601/34 |
| 5,823,975 A * | 10/1998 | Stark et al. | 600/595 |
| 5,840,047 A | 11/1998 | Stedham | |
| 6,184,797 B1 * | 2/2001 | Stark et al. | 340/870.07 |
| 6,436,058 B1 * | 8/2002 | Krahner et al. | 600/587 |
| 6,462,431 B1 * | 10/2002 | Woo | 307/9.1 |
| 6,500,138 B1 * | 12/2002 | Irby et al. | 602/26 |
| 6,517,503 B1 | 2/2003 | Naft et al. | |
| 6,872,187 B1 * | 3/2005 | Stark et al. | 602/16 |
| 6,979,304 B2 * | 12/2005 | Nijenbanning et al. | 602/16 |
| 7,172,567 B2 * | 2/2007 | Lidolt et al. | 602/23 |
| 7,235,058 B2 * | 6/2007 | Doty et al. | 602/16 |
| 2002/0183673 A1 * | 12/2002 | Naft et al. | 602/16 |
| 2003/0212356 A1 * | 11/2003 | Scorvo | 602/20 |
| 2006/0224246 A1 * | 10/2006 | Clausen et al. | 623/24 |

FOREIGN PATENT DOCUMENTS
EP 0 141 640 5/1985

\* cited by examiner

*Primary Examiner* — Patricia Bianco
*Assistant Examiner* — Brandon L Jackson
(74) *Attorney, Agent, or Firm* — Whitham Curtis Christofferson & Cook, PC

(57) ABSTRACT

The use of an orthopedic aid with two parts (15, 16) which are movable relative to one another and with a locking device for locking the two parts (15, 16) in a predetermined relative position and for unlocking the parts (15, 16) in order to permit movement of the parts (15, 16) with respect to one another is made much safer by virtue of the fact that at least one signaling arrangement (36, 40, 41, 42) is provided which emits a particular signal for the locking state or upon unlocking of the locking device. The risk of accidents due to the parts (15, 16) being incorrectly locked is at least substantially reduced.

17 Claims, 7 Drawing Sheets

ORTHOPEDIC AID WITH A LOCKING DEVICE

BACKGROUND OF THE INVENTION

1. Field of the Invention

The invention relates to an orthopedic aid with two parts which are movable relative to one another and with a locking device for locking the two parts in a predetermined relative position and for unlocking the parts in order to permit movement of the parts with respect to one another.

2. Background Description

Orthopedic aids of this kind are used in many applications intended to provide compensation for temporary or permanent weaknesses of the human body and to enable functions that it would otherwise not be possible to perform. This is achieved by the orthopedic aid providing a supporting function in which, in a defined position of the parts of the aid, these parts are locked with respect to one another, and the locked position of the two parts with respect to one another corresponds to a position of use in which the patient concerned requires the supporting function afforded by the orthopedic aid. A preferred application of an orthopedic aid of this kind is in its design as an orthotic joint, where, for example, the parts of the orthotic joint connected to one another by a hinge can be locked in an extended position, for example in order to permit the function of a limb in the extended and locked position of the orthotic joint. To get to a rest position, the locking device has to be unlocked. In known orthotic knee joints, this is done, for example, by means of a Bowden cable with which the locking device can be unlocked, so that the knee joint can be flexed, for example in order to allow the patient to get to the seated position. After the patient stands up, the orthotic knee joint has to move back into the extended, locked position. If the locked position is not reached and the patient fails to notice this, there is a considerable risk of an accident happening since, when a load is placed on the orthotic knee joint that is assumed to be locked, the latter may buckle, and the buckling cannot be controlled by the patient because of the weakness of the joint. As a result, the patient may suffer a fall. For this reason, the patient has to pay particular care to ensure that the orthopedic aid is in fact really locked, for example by waiting for a sound, which indicates that the locking device has engaged, before placing any load on the aid.

SUMMARY OF THE INVENTION

The present invention starts out from the problem that, as a result of a certain degree of carelessness on the part of the user of the orthopedic aid, it is not ascertained whether the locking device is definitely locked, and, consequently, there is a risk of an accident happening. The object of the present invention is therefore to avoid, as far as possible, a situation in which the wearer of the orthopedic aid is adversely affected by incomplete locking of the parts of the aid with respect to one another.

Starting out from this problem, an orthopedic aid of the type mentioned at the outset is distinguished, according to the invention, by the fact that at least one signaling arrangement is provided which emits a particular signal for the locking state or upon unlocking of the locking device.

The signaling arrangement according to the invention thus generates a particular signal which clearly indicates the locking state (locked or unlocked) to the user of the orthopedic aid or provides a warning signal if the locking device is unlocked. In the event of inadvertent unlocking of the orthopedic aid, the latter is of importance for warning the user that the locked state no longer exists, so that, if appropriate, the user restores the locked state if unlocking has inadvertently occurred.

In a preferred embodiment of the device of the invention, the orthopedic aid has at least one detection arrangement for detecting the locking state (locking and/or unlocking) of the two parts and for emitting a signal indicating the locking state. The locking state is preferably displayed as an acknowledgement signal for the user and informs him that the intended locking has actually taken place, so that it is safe to place a load on the orthopedic aid.

The signaling arrangement can also be designed to emit a signal upon unlocking and serve as a warning signal in the event of inadvertent unlocking of the locking device.

The emitted signal can be visual, acoustic, tactile and/or mechanical. The signals are preferably emitted in several forms in order to avoid a situation where the signal is not seen or not heard. In addition to the visual and acoustic emission of the signal, it can also be emitted mechanically in the form of vibrations or in tactile form, for example if a handgrip, for example of a walking aid, has to be grasped in order to use the orthopedic aid.

The detection arrangement can be designed to generate the signal electrically as a function of the locking state. In this case, the locking state itself is also preferably detected by electrical means. This can be done, for example, by the locking device having a movable locking pin whose position can be detected by the detection arrangement.

In a preferred embodiment, the locking device according to the invention can be designed to be actuated electromechanically to permit unlocking. In the case of a locking device working with a locking pin, the locking pin in this case can be arranged such that it can be drawn into a magnet coil to permit unlocking. The actuation is thus in the manner of an electromagnet.

The detection arrangement is preferably designed for electrical scanning of the position of the locking pin. This scanning can be done in the manner of a potentiometer or preferably by inductance.

By virtue of the electromechanical unlocking of the locking device, it is possible to ensure that the unlocking is possible electromechanically only when the parts of the orthopedic aid are loaded in accordance with the locked position, so that unlocking is not possible if a force not corresponding to the position of the parts in the locked state is exerted on said parts. The orthopedic aid can be designed specifically as an orthotic joint in which the parts of the orthosis can be locked in an extended position, wherein an electromagnetic actuating arrangement with a low actuating force of not more than 2 N is provided, and the orthotic joint in the extended position has a slight play, allowing a freedom of movement of the locking mechanism in the loading of the orthotic joint pertaining to the extended position, whereas, in the event of a load exerting a turning moment of the orthotic joint, the locking mechanism cannot be unlocked by the actuating arrangement on account of frictional forces. The actuating force of the electromagnetic actuating arrangement is preferably $\leq 1$ N.

In a further preferred embodiment, the locking device is actuated by wireless transmission of an actuating signal. In the case of an orthotic joint for the leg, it is generally necessary to use a walking aid in the form of crutches or in the form of a walking frame. In this case, it is extremely advantageous if the actuating signal for wireless transmission of the command signal can be triggered on a handgrip of the walking aid.

Conversely, the signal of the signaling arrangement according to the invention can also be sent by wireless transmission to the walking aid, if said walking aid preferably has a visual and/or acoustic signal display arrangement and/or a handgrip of the walking aid is provided with a vibrator that can be actuated by the signal.

It is therefore possible to use the walking aid to trigger the actuation of the locking device, in particular for unlocking, and also to use the walking aid to receive the acknowledgement signal or warning signal emitted by the signaling arrangement according to the invention.

BRIEF DESCRIPTION OF THE DRAWINGS

The invention is explained in greater detail below with reference to an illustrative embodiment shown in the drawing, in which.

DETAILED DESCRIPTION OF A PREFERRED EMBODIMENT OF THE INVENTION

Figure 1:
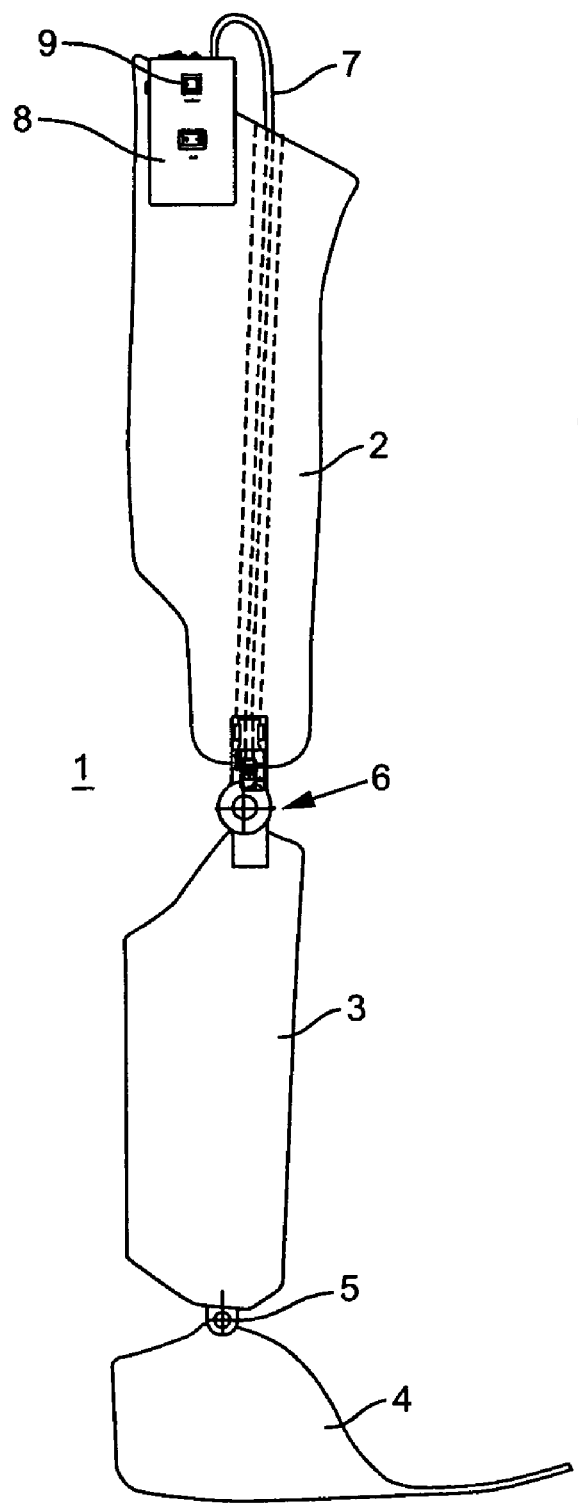
FIG. 1 shows a side view of an orthotic leg device according to one embodiment of the invention.

The orthotic leg device 1 shown in FIG. 1 has a thigh shell 2, a below-knee shell 3 and a foot shell 4. The below-knee shell 3 and the foot shell 4 are connected to one another via a pivot hinge 5. Arranged between the thigh shell 2 and the below-knee shell 3 there is a lockable hinge 6 which is connected via a connection cable 7 to a control module 8 which can be attached on the top of the thigh shell 2.

Flat stiffening rods (not shown in FIG. 1) can be inserted into the hinge 6 and can be connected to the thigh shell 2 and below-knee shell 3.

The hinge 6 can be locked in the extended position shown in FIG. 1 and can be unlocked by means of an unlocking key 9 on the control module 8.

Figure 2:
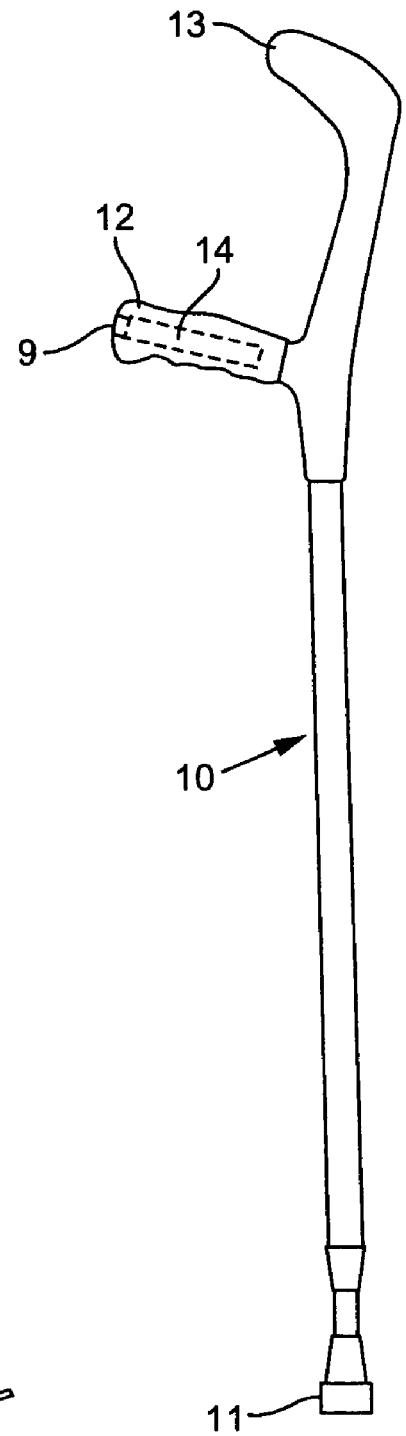
FIG. 2 shows a walking aid in the form of a crutch belonging to the orthotic leg device according to FIG. 1.

FIG. 2 shows a walking aid 10 in the form of a bar-shaped crutch which, at the bottom end, has a rubber part 11 for placing on the ground and, at the upper end, has a handgrip 12 and a forearm support 13. A trigger switch 9' is integrated into the handgrip 12 and can be actuated from the end face of the handgrip 12, preferably by thumb, and acts on a transmitter 14 which then can send an actuating signal for the control module 8. The control module 8 is in this case set up for radio reception.

The structure of the hinge 6 is shown in greater detail in FIGS. 3 through 7. The hinge 6 consists of two hinge parts 15, 16 which are pivotably connected to one another via the pivot 17.

The part 15 is designed as the lower part of the hinge, with a downwardly open receiving compartment 18 for a flat stiffening rod, which is connected to the below-knee shell 3. Correspondingly, the part 16 has an upwardly open receiving compartment 19 for receiving a stiffening rod for the thigh shell 2.

Figure 3:
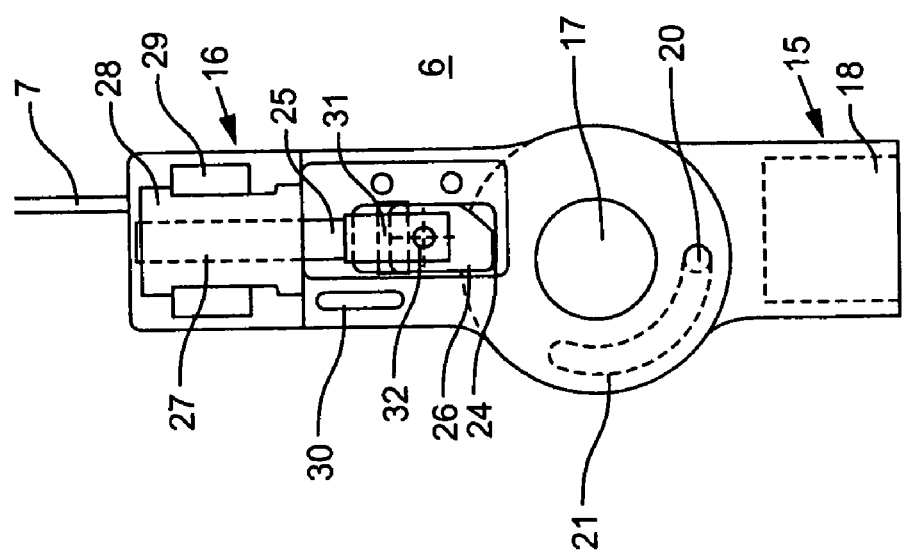
FIG. 3 is a detail of a hinge of the orthotic device according to FIG. 1, shown in a side view and in the locked state.
Figure 7:
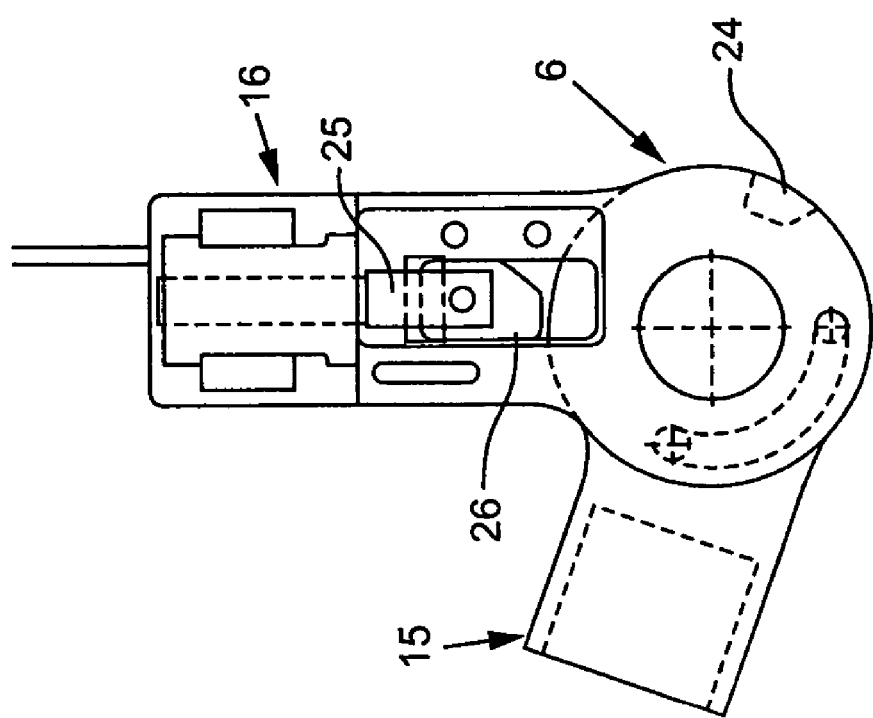
FIG. 7 shows a side view of the hinge according to FIG. 5, in the flexed state.

The lower part 15 of the hinge is provided with a guide pin 20 which can be moved in a guide groove 21 forming approximately a quarter of a circle and thus forms abutments for the extended position according to FIG. 3 and for a flexed position of the hinge 6 according to FIG. 7.

In the area of the pivot 17, the lower part 15 and upper part 16 of the hinge both form circular, eye-shaped end portions 22, 23 which are fitted in one another to form the pivot 17. The end portion 22 of the lower part 15 of the hinge is provided with a radial recess 24 into which a locking pin 25 engages with a lower end 26 shaped to match the recess 24, in order to lock the lower part 15 and upper part 16 of the hinge together in the extended position shown in FIGS. 3 and 4. At its upper end, the locking pin 25 merges into a cylindrical core 27 which is axially movable in the interior of an electrical coil 28. The electrical coil 28 is fixed in a mounting 29 in the upper part of the hinge. The position of the locking pin 25 can be detected by means of a sensor 30 arranged together with the locking pin 25 in the upper part 16 of the hinge and extending parallel to said locking pin 25. A permanent magnet 31 connected to the locking pin 25 and interacting with the sensor 30 extends transversely with respect to the locking pin 27 and its magnetic field can be detected by the sensor 30, which can be a Hall sensor. In the locked position shown in FIG. 3, the sensor 30 does not detect any magnetic field of the permanent magnet 31. If the locking pin 25 moves upward because it is drawn, by a flow of current, through the coil 28 and into the interior of the latter, the field of the permanent magnet 31 reaches the area of the sensor 30, which thus detects the unlocked state. Both the current for the coil 28 and the output signal of the sensor 30 are transmitted from/to the control module 8 via the connection cable 7.

Figure 4:
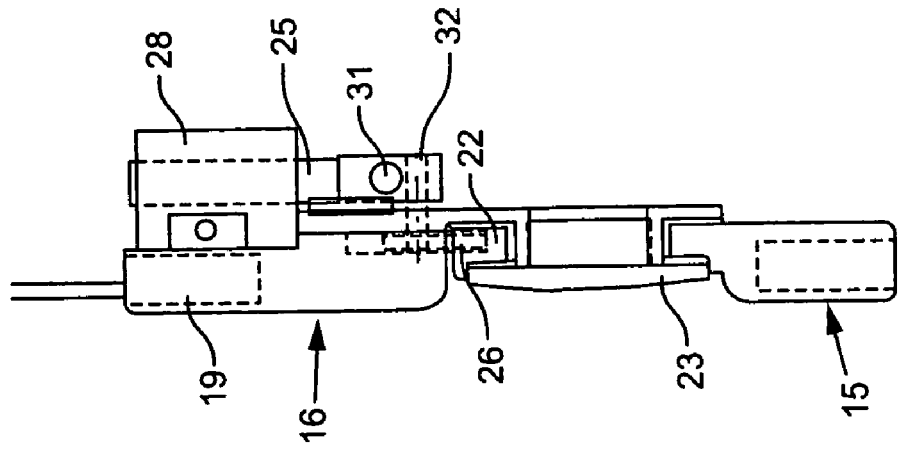
FIG. 4 shows the hinge according to FIG. 3 in a view from behind.

FIG. 4 illustrates that the endpiece 26 of the locking pin 25 can be shifted axially sideways and is connected to the locking pin 25 via a connecting pin 32.

Figure 6:
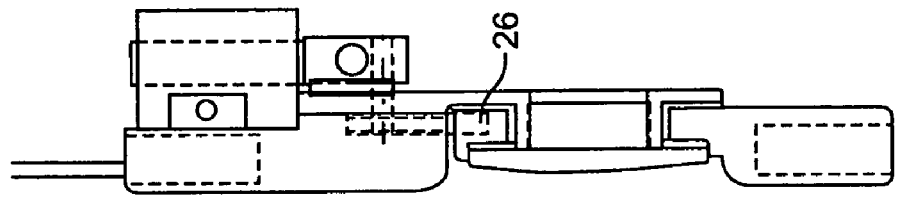
FIG. 6 shows the view according to FIG. 4, with the hinge in the unlocked state.
Figure 5:
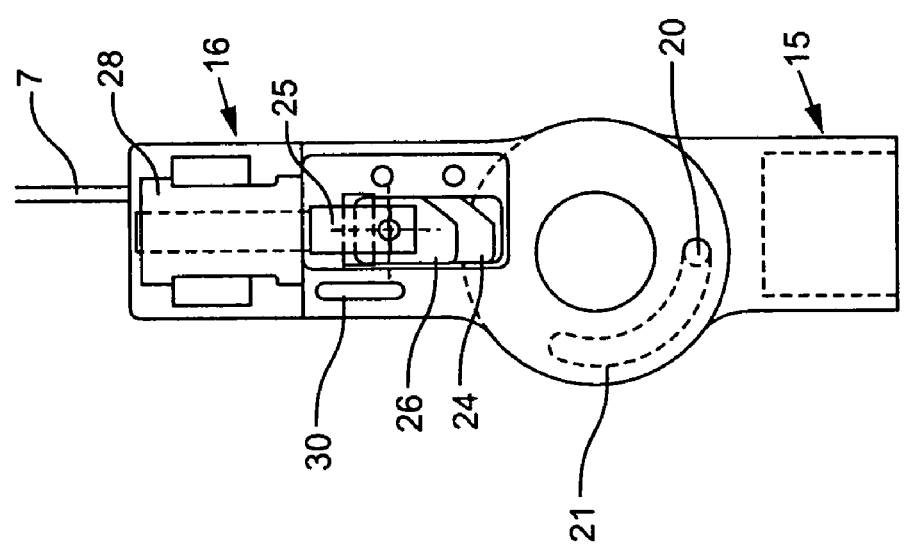
FIG. 5 shows the view according to FIG. 3, with the hinge in the unlocked state.

FIGS. 5 and 6 show the hinge 6 in the unlocked state. Current flows through the coil 28 via the connection cable 7, and the coil 28 acts as electromagnet for the locking pin 25 which is drawn into the interior of the coil 28 (upward as shown in the drawing) and pulls the end 26 connected to it from the associated recess 24, so that the lower part 15 of the hinge is now pivotable relative to the upper part 16 of the hinge, specifically within the guide 20, 21 defined by the guide pin 20 and the guide groove 21.

FIG. 7 shows the flexed end position of the hinge 6, as is adopted when the user sits down. The end 26 of the locking pin 25 slides on the cylindrical peripheral surface of the end portion 22 of the lower part 15 of the hinge. If the user moves from the flexed state according to FIG. 7 to the extended state according to FIGS. 3 through 6, the lower end 26 of the locking pin 15 slides, under the effect of gravity, on the peripheral surface of the end portion 22 until the lower end 26 drops into the recess 24 in the fully extended position and actuates the lock according to FIGS. 3 and 4.

Figure 8:
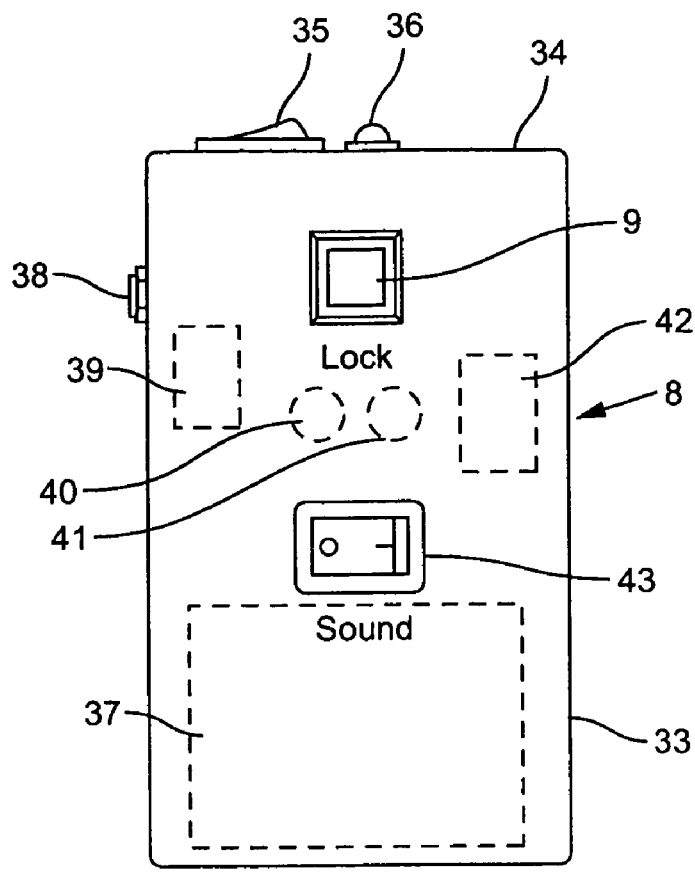
FIG. 8 shows a side view of a control module with an unlocking key.
Figure 9:
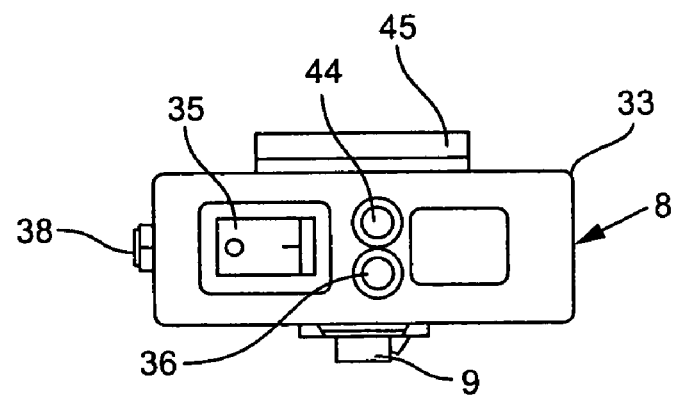
FIG. 9 shows a plan view of the control module according to FIG. 8.

The control module 8 illustrated in FIGS. 8 and 9 has the key 9, for unlocking the hinge 6, at a position convenient to reach. The control module is provided with a rectangular, flat housing 33 on whose narrow top face 34 there is a main switch 35 with a warning light 36. The housing 33 contains, on the underside, a battery 37, which can be recharged via a charge socket 38 arranged on a narrow side wall. The control module 8 further includes a short-time control 39 and two sound generators 40, 41 and a vibrator 42. The sound generators 40, 41 can be switched off via a switch 43 in order to suppress an acoustic signal in certain situations where the latter would be undesirable.

FIG. 9 shows that the top face 34 of the housing 33 is provided with a further control light 44 indicating the state of charging of the battery 37. The housing 33 is moreover provided with a clip bracket 45 with which it can be clipped onto the top edge of the thigh shell 2.

Figure 10:
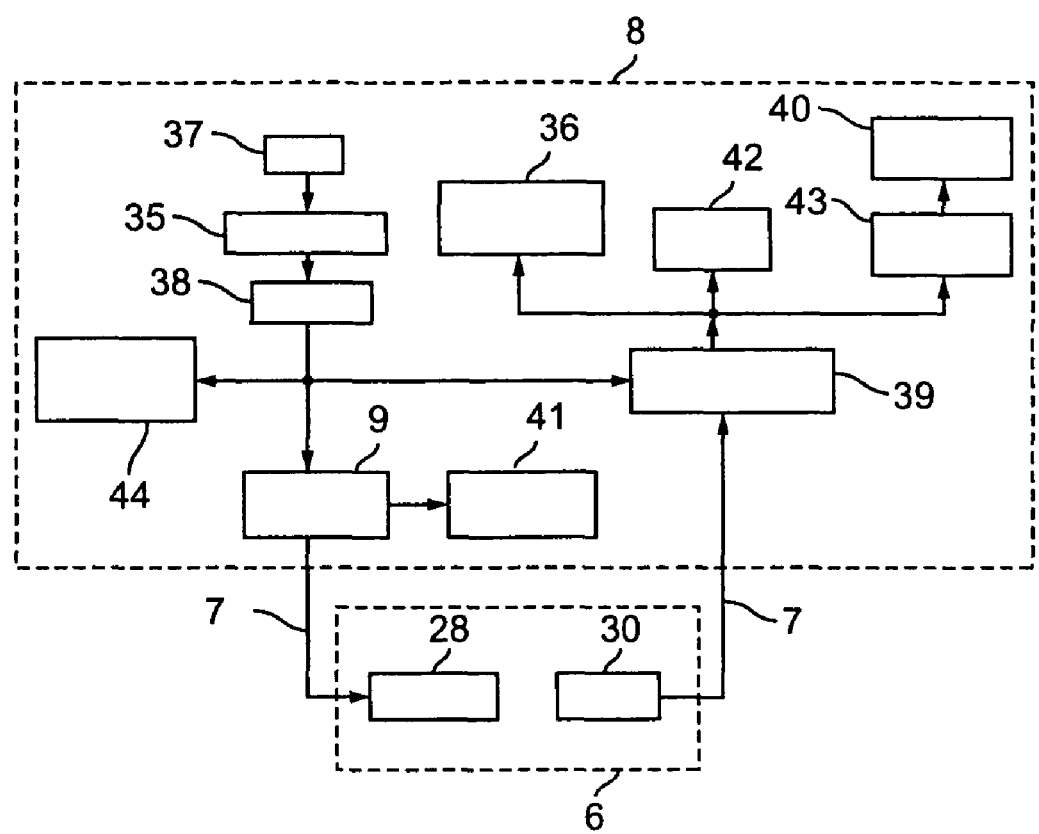
FIG. 10 shows a block diagram of the electrical parts of the orthotic leg device according to FIG. 1, equipped with a control module according to FIGS. 8 and 9.

The block diagram in FIG. 10 shows the functional circuitry in the control module 8 and the signals transmitted to the hinge 6 via the connection cable 7.

The battery 37 is connected via the main switch 35 to the charge socket 38 and to the key 9 for unlocking the hinge 6. When the key 9 is actuated, the sound generator 41 is triggered and emits a warning sound for unlocking. With the main switch 35 switched on, the state of charging of the battery 37 is indicated by the control light 44; for example, the control light 44 does not light if the state of charging of the battery 37 is sufficient. By actuating the key 9, a current is conveyed via the connection cable 7 into the coil 28 in the hinge 6, as a result of which the hinge is unlocked.

If the sensor 30 of the hinge 6 detects that the locking pin 25 has dropped back into the locked position, this output signal of the sensor 30 is transmitted via the connection cable 7 to the control module 8 and there, via the short-time control 39, emits acknowledgement signals, namely by the control light 36 lighting up via the short-time control 39, actuation of the vibrator 42, and actuation of the sound generator 40, unless the latter has been switched off via the switch 43.

Figure 11:
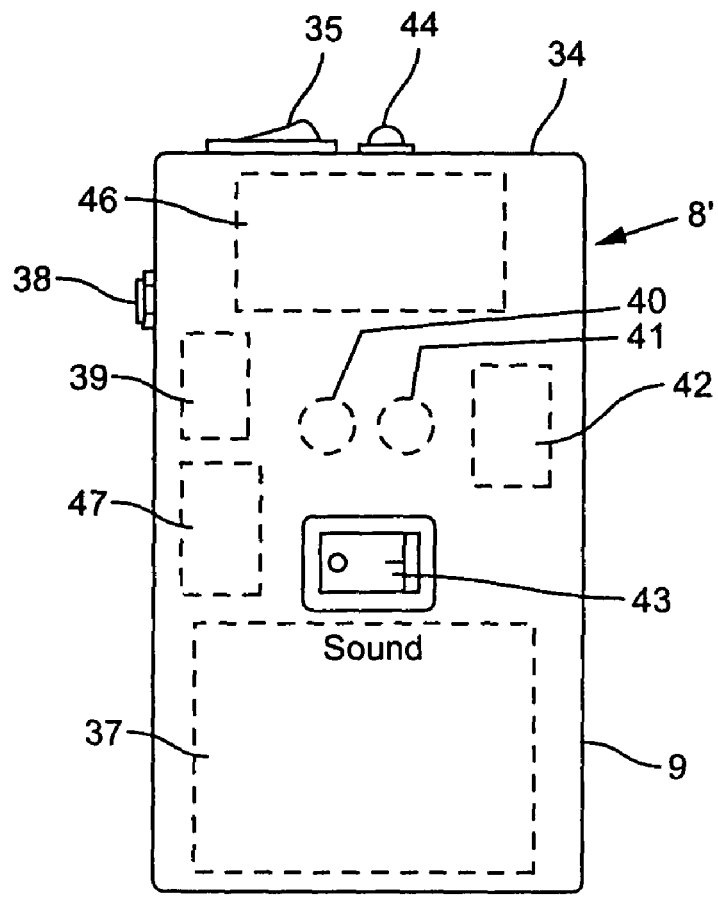
FIG. 11 shows a control module for the orthotic leg device according to FIG. 1, with wireless control.
Figure 12:
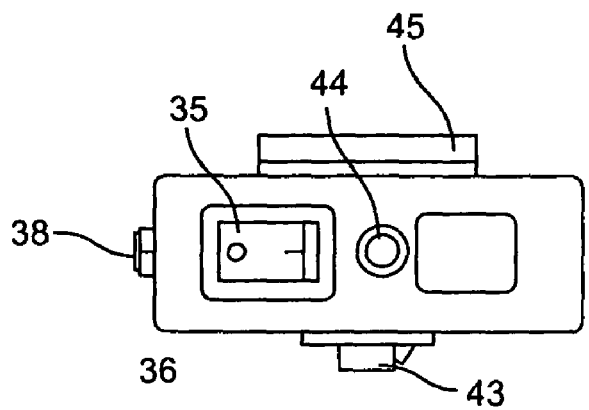
FIG. 12 shows a plan view of the control module according to FIG. 11.

FIGS. 11 and 12 show the control module 8' for radio reception of an actuating signal triggered by the transmitter 14 of the walking aid 10 and is therefore additionally provided with a radio receiver 46 and a switching relay 47 instead of with the switch 9. Of course, it is also possible to provide, in addition to the radio receiver 46 and the switching relay 47, the possibility of unlocking via the key 9 in the control module 8, 8'.

In the embodiment shown in FIGS. 11 and 12, the fact that the switch 9 is omitted also means that the corresponding control light 36 is dispensed with, so that only the control light 44 for the state of charging of the battery 37 is now located on the top face 34 of the housing 9.

Otherwise, the control module 8' is identical to the control module 8.

The invention claimed is:

1. An orthopedic aid which is used by a patient for walking and which provides a supporting function for the human body, comprising:
   two parts which are rotatable relative to one another;
   a locking device for locking the two parts in an extended position so that a rotation of the two parts relative to one another is blocked during standing and walking and for manually unlocking the two parts to permit rotation of the two parts with respect to one another in a rest position,
   wherein said locking device is operable by a user of the orthopedic aid;
   means for automatically detecting locking of said locking device; and
   a signaling arrangement which emits a signal, responsive to said means for automatically detecting said locking, for alerting the user of the orthopedic aid that the locking of said locking device has taken place.

2. The orthopedic aid as claimed in claim 1, wherein the locking device has a movable locking pin whose position is detected by the means for detecting.

3. The orthopedic aid as claimed in claim 2, wherein the movable locking pin is arranged such that it can be drawn into a magnet coil to permit unlocking.

4. The orthopedic aid as claimed in claim 2, wherein the detection arrangement is designed for electrical scanning of a position of the locking pin.

5. The orthopedic aid as claimed in claim 1, wherein the locking device is actuated by wireless transmission of an actuating signal.

6. The orthopedic aid as claimed in claim 5, wherein an actuating signal for wireless transmission of a command signal is triggered on a handgrip of a walking aid.

7. The orthopedic aid as claimed in claim 5, wherein the signal of the signaling arrangement is sent by wireless transmission to a walking aid.

8. The orthopedic aid as claimed in claim 7, wherein the walking aid has a visual and/or acoustic signal display arrangement.

9. The orthopedic aid as claimed in claim 7, wherein a handgrip of the walking aid is provided with a vibrator that can be actuated by the signal of the signaling arrangement.

10. The orthopedic aid as claimed in claim 1, wherein the signaling arrangement emits a signal upon unlocking.

11. The orthopedic aid as claimed in claim 1, wherein said signaling arrangement provides a signal which is visual, acoustic, tactile and/or mechanical.

12. The orthopedic aid as claimed in claim 1, wherein said means for detecting includes a detection arrangement designed to generate the signal electrically as a function of the locking state.

13. The orthopedic aid as claimed in claim 1, wherein the locking device is actuated electromechanically to permit unlocking.

14. The orthopedic aid as claimed in claim 1 further comprising an electromagnetic actuating arrangement with a low actuating force of not more than 2 N, wherein the locking device, when in the extended position, has a slight play, allowing a freedom of movement of the locking mechanism in the loading pertaining to the extended position, whereas, in the event of a load exerting a turning moment on the locking device, the locking device cannot be unlocked by the actuating arrangement on account of frictional forces.

15. An orthopedic aid as in claim 1, further comprising a safety function for operation of the supporting function, wherein said signal confirms an observation by the user that the orthopedic aid is locked.

16. An orthopedic aid which is used by a patient for walking and which provides a supporting function for the human body, comprising:
   two parts which are rotatable relative to one another;
   a locking device for locking the two parts in an extended position so that a rotation of the two parts is blocked during standing and walking and for manually unlocking the two parts to permit rotation of the two parts with respect to one another in a rest position, wherein said locking device is operable by a user of the orthopedic aid;
   means for automatically detecting the locking state of said locking device; and
   a signaling arrangement which emits a signal, responsive to said means for automatically detecting the locking state, upon unlocking as a warning signal in the event of inadvertent unlocking of the locking device.

17. An orthopedic aid as in claim 16, further comprising a safety function for operation of the supporting function, wherein said signal contradicts an observation by the user that the orthopedic aid is locked.

* * * * *